United States Patent [19]

Daniels et al.

[11] 4,361,901
[45] Nov. 30, 1982

[54] MULTIPLE VOLTAGE X-RAY SWITCHING SYSTEM

[75] Inventors: Herbert E. Daniels, Brown Deer; Frank Bernstein, Milwaukee; Thomas W. Lambert, Dousman; Norbert J. Pelc, Wauwatosa, all of Wis.

[73] Assignee: General Electric Company, Schenectady, N.Y.

[21] Appl. No.: 208,095

[22] Filed: Nov. 18, 1980

[51] Int. Cl.³ .............................................. G03B 41/16
[52] U.S. Cl. .................................. 378/106; 378/110; 378/112
[58] Field of Search ............... 250/401, 402, 403, 404, 250/408, 409, 413

[56] References Cited

U.S. PATENT DOCUMENTS

| | | | |
|---|---|---|---|
| 3,633,029 | 1/1972 | Duffy | 250/403 |
| 3,904,874 | 9/1975 | Amtmann | 250/405 |
| 4,104,526 | 8/1978 | Albert | 250/403 |

Primary Examiner—Craig E. Church
Attorney, Agent, or Firm—Ralph G. Hohenfeldt

[57] ABSTRACT

X-ray pulses at two different photon energy levels are produced with an x-ray tube that has an adjustable resistor element in a circuit that connects the anode and filament of the tube to a high voltage supply. Two bias voltage supplies are connected in additive fashion between a control grid element of the tube and its filament to enable control of voltage drop and current through the tube. Switch means are provided to selectively shunt either or both bias voltage supplies in a repeatable order to thereby alter the bias voltage on the control grid and enable producing x-ray pulses having energies corresponding with the voltage drop and current through the tube at a selected bias voltage in accordance with the load line on the anode characteristic curve plot of the tube as determined by the value of the adjustable resistor element.

14 Claims, 10 Drawing Figures

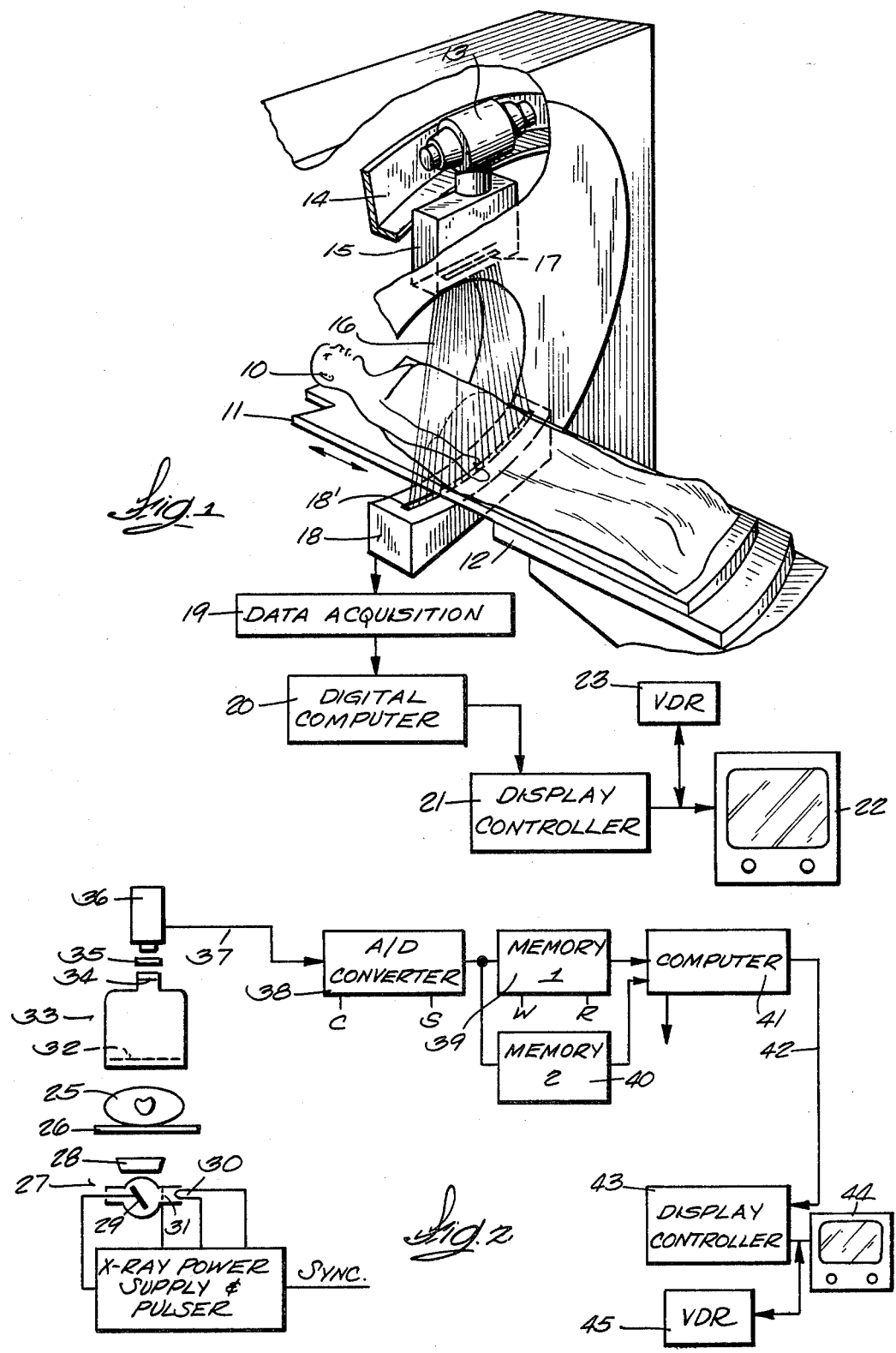

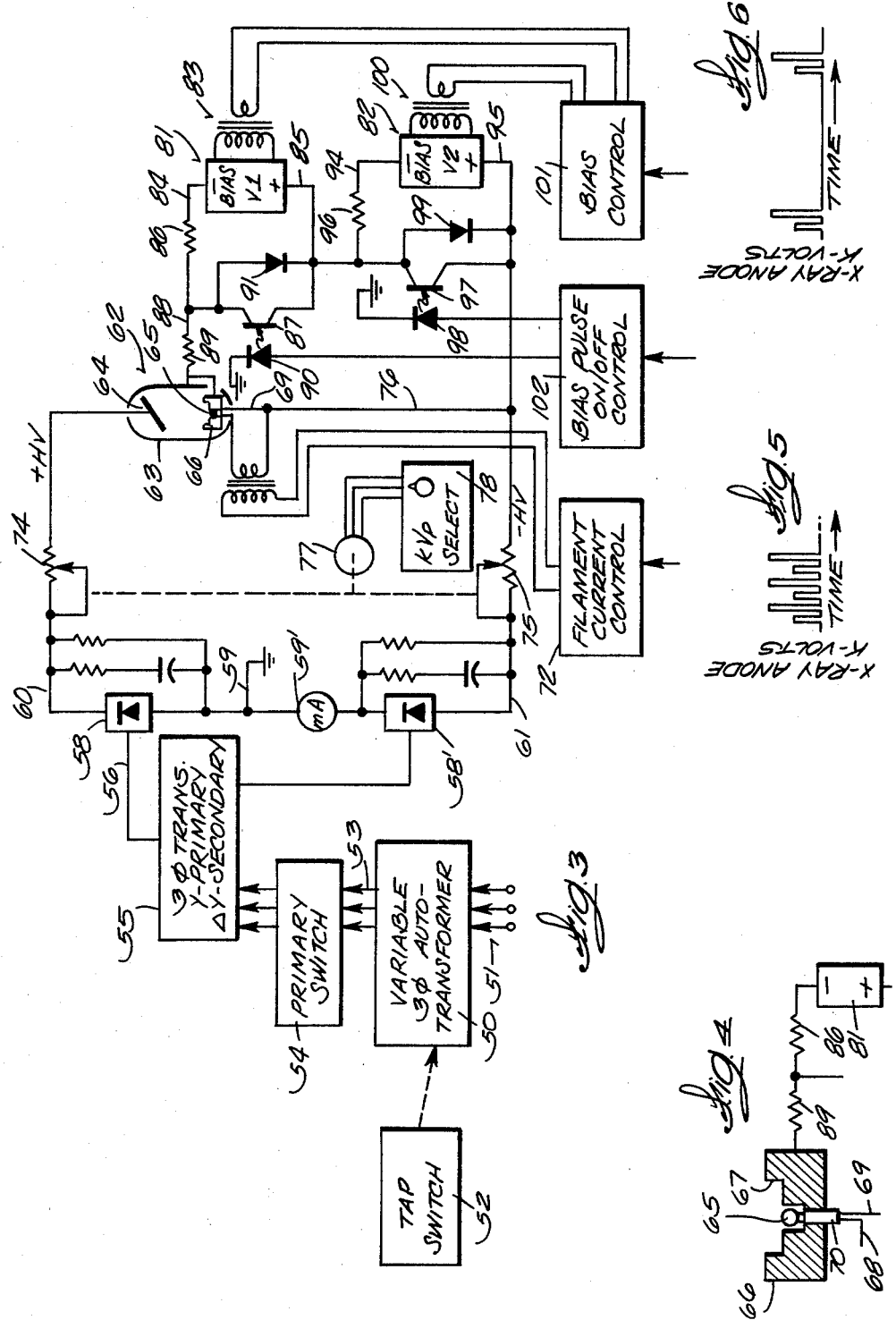

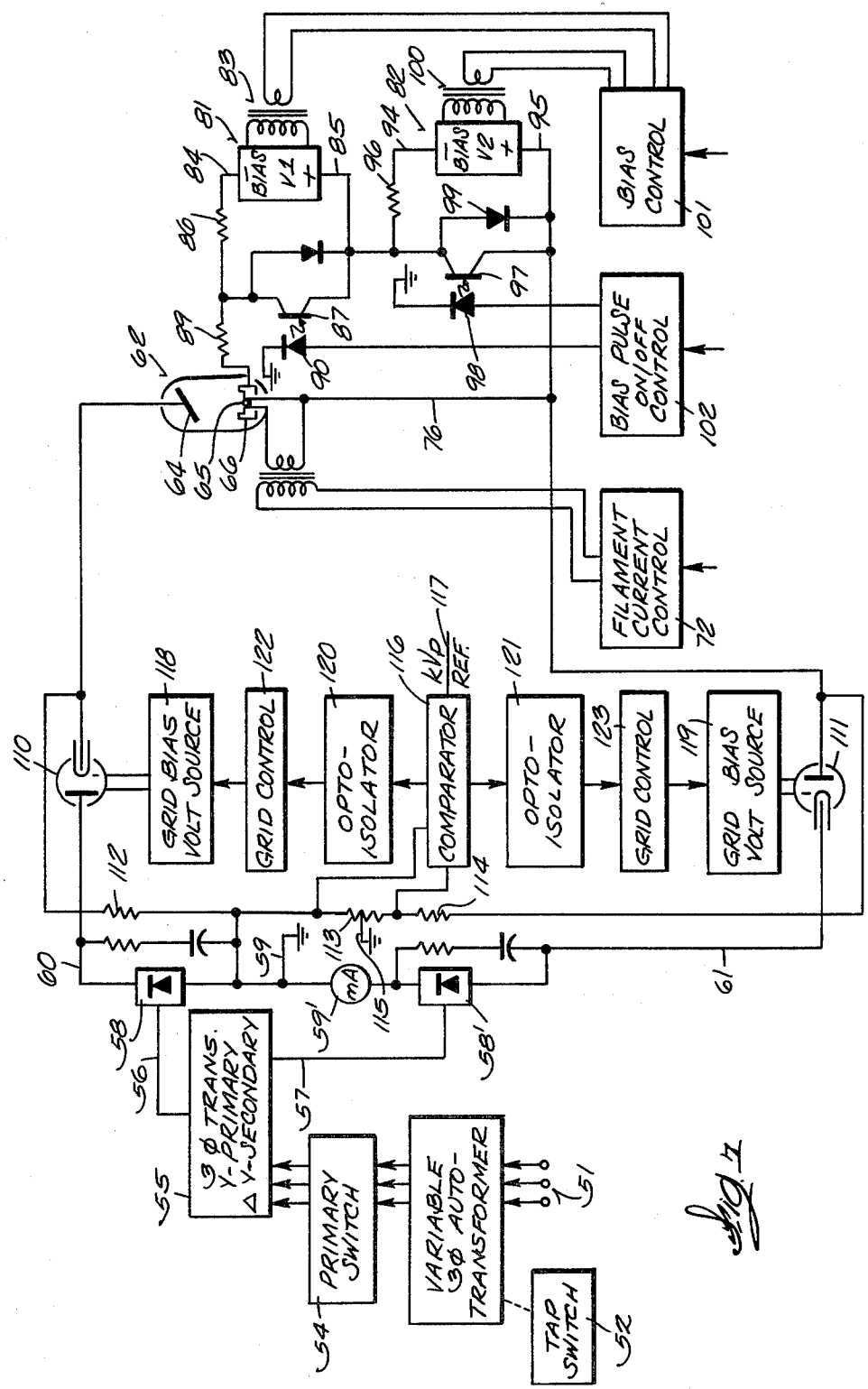

MULTIPLE VOLTAGE X-RAY SWITCHING SYSTEM

BACKGROUND OF THE INVENTION

This invention relates to diagnostic x-ray apparatus generally and, in particular, to a system for controlling an x-ray tube to emit pulses of x-rays of different average energies in rapid sequence.

An occasion for using a sequence of x-ray pulses at different energies is when it is desirable to selectively suppress or enhance the contribution to an x-ray image from a certain material. One instance is the imaging of body structures containing small amounts of an x-ray opaque dye, for example an iodine compound. Applications include the imaging of blood vessels opacified by intravenous injections of dye, or the imaging of tumors and/or organs slightly opacified by a dye. In normal x-ray images, the low image contrast of the iodine-containing region can be masked by overlying and underlying bone or soft tissue structures and be made very difficult to see. Energy subtraction, as the method of combining images at different x-ray energies is called, can enhance the contrast of one material, for example iodine, with respect to that of other materials, for example bone and/or soft tissue, and greatly improve the visibility of the structures of interest. Another application of energy subtraction may be in separating the contributions to an image due to bony structures from those due to soft tissue structures, for example in chest imaging. A sequence of x-ray pulses at different energies can also be used in computerized tomographic (CT) imaging. In CT, the x-rays of different energies can be used to provide information on the chemical composition as well as density of a transverse section. The use of pulses at different energies also has the benefit of reducing certain beam-hardening artifacts in CT.

An alternative to energy subtraction for the improved visualization of administered contrast agents is temporal subtraction. In temporal subtraction images taken before and after the injection of the iodinated dye are subtracted. The basic limitation of temporal subtraction is that the images being combined are separated in time by several seconds, and any motion that occurred between the acquisition of the two images will result in mis-registration artifacts in the image. Further, temporal subtraction is not well suited to imaging contrast-producing materials that are slowly or not at all time varying, for example, bones or iodine dye sequestered by tumors. However, if the images for energy subtraction are gathered in rapid time sequence little or no motion could have occurred during the image acquisition time and subtraction images with no mis-registration artifacts can be produced. What is required, then, is a means by which the average photon energy of the x-ray beam can be switched very quickly.

The computational methods and theoretical aspects of energy subtraction are described in the literature. Theories for energy subtraction using two or three different x-ray energies have been developed. This application describes in detail an improved method for producing x-ray pulses of two energies in rapid sequence. It is understood that the same concept could be used to produce pulses with three different x-ray spectra in rapid sequence.

The average energy of an x-ray beam can be affected by added x-ray filtration, and multi-energy methods using switching filters have been described. However, in order to change the x-ray energy significantly, heavy filtration is required and the resulting x-ray intensity is greatly reduced. A preferred method is to change both the x-ray filtration as well as the voltage at which the x-rays are produced.

Ideally, the required x-ray switching system should rapidly change both the x-ray tube peak kilovoltage (kVp) as well as the tube current (mA). It is preferred to have a higher mA for the lower kVp pulses. Prior art switching circuits which change the kVp only through the use of a variable high voltage control, such as a high voltage tetrode, result in an mA change in the wrong direction. That is, the lower the kVp applied to the tube, the lower the tube current. If the system is set up so that the highest kVp pulse has a current that does not exceed the tube rating, the lower kVp pulses with the lower current will likely produce a less than optimum total intensity. Changing mA in the traditional manner, that is, by changing x-ray tube filament current, is too slow due to the thermal lag of the filament.

SUMMARY OF THE INVENTION

An object of the present invention is to provide an x-ray tube switching circuit which enables rapid and accurate changing of both the x-ray tube peak kilovoltage and the tube current in a plurality of steps and at high repetition rates.

Briefly stated, in accordance with the invention, an x-ray tube comprising an anode target, a filament and a control element, commonly called a grid is used. In the embodiment which is described first, two negative bias voltage sources are provided each of which is adapted for providing a different voltage. In this embodiment, the bias voltage sources are arranged in what is essentially a series circuit between the control element and cathode filament of the tube. Shunting switches are connected across the output of the bias voltage sources. In one operational mode, when both shunting switches are non-conducting, the sum of the bias voltages is applied between the control grid and filament of the tube to thereby make the x-ray tube nonconductive, or, in other words, to cut off cathode electron emission. Dynamic characteristics of the x-ray tube are predetermined by inserting a selected amount of resistance in the anode-to-cathode high voltage supply circuit of the x-ray tube. The dynamic characteristics of the x-ray tube are plotted in a manner which is typical of vacuum tubes. The plot shows the x-ray tube current and voltage drop across the tube that will prevail at various bias voltages for a variety of load lines.

Thus, when the first bias voltage source is shunted the second bias voltage source remains effective and the voltage drop and current can be determined from the dynamic characteristic plot. By selecting an appropriate bias level for the second bias source, the x-ray tube current and voltage can be determined.

When both switching circuits are triggered into a conductive state and both bias voltage sources are shunted, near zero bias voltage is applied to the x-ray tube control grid. The x-ray tube current then changes as desired, as compared with the previously discussed biasing conditions, and the tube voltage changes as well.

How the new dual voltage x-ray tube switching system is implemented and typical x-ray apparatus in which it can be used advantageously will now be described in reference to the drawings.

FIG. 1 is a partial perspective view of a computed scanned projection radiography system in which the new dual x-ray energy high voltage switching system may be used;

FIG. 2 is a block diagram of a digital fluoroscopy system in which the dual switching system may be used;

FIG. 3 is a diagram of an x-ray tube power supply circuit which incorporates the new dual energy switching system;

FIG. 4 is a diagram of the cathode structure, comprised of a control element in the form of a focusing cup and a filament, which is used in the x-ray tube of the FIG. 3 circuit;

FIG. 5 is the x-ray pulse timing diagram pertinent to the computed projection radiography system in FIG. 1;

FIG. 6 is an x-ray pulse timing diagram pertinent to the digital fluoroscopy system depicted in FIG. 2;

FIG. 7 is an alternative embodiment of the system shown in FIG. 3;

DESCRIPTION OF A PREFERRED EMBODIMENT

Figure 8:
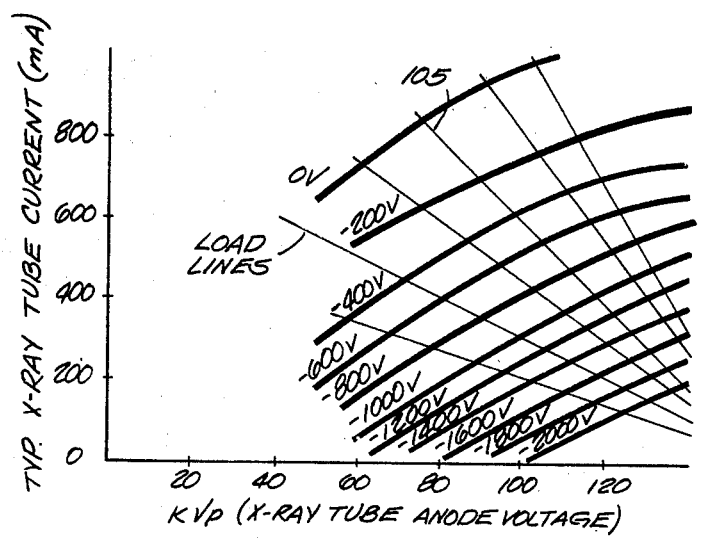
FIG. 8 is a plot of the dynamic characteristics of a typical x-ray tube used in the new bias voltage switching system.

The apparatus shown in FIG. 1 is for making computed axial tomography and computed scanned projection radiography examinations of a patient. Computed scanned projection radiography provides an image of a patient's anatomy which can be displayed on a television monitor and which is analogous to the kind of image which is obtained in conventional radiography where an x-ray beam is projected through a body and is recorded on film.

In the FIG. 1 apparatus, the patient 10 being examined is supine on an x-ray transmissive table top 11. The top 11 is mounted on a support 12 for being translated at a constant rate in the longitudinal direction, that is, lengthwise of the patient. An x-ray tube, not visible in FIG. 1, is contained in a casing 13 and is shown in a fixed position above the patient for the purposes of conducting computed scanned projection radiography. The tube casing is mounted on a ring 14 in this particular machine for being rotated around the patient when computed axial tomography is to be performed. An x-ray beam collimator 15, is coupled to the x-ray tube casing for shaping the emerging x-ray beam into a thin fanshaped or diverging x-ray beam 16. When computed projection radiography is being conducted, the x-ray beam projects transversely through the patient and the direction in which the patient or source and detector are moved relatively during the scan is perpendicular to the plane of the beam. A slot 17 in the bottom of the collimator symbolizes the cross-sectional shape of the beam.

An x-ray detector 18 is supported on ring 14 below the patient for orbiting around the patient jointly with the x-ray tube casing when computed axial tomography is being performed. However, for scanned projection radiography which is presently being considered, the detector and x-ray tube are held in a fixed position. The detector 18 may be one of the well-known gas-filled ionization or solid state scintillation types which are used in computed axial tomography. Detectors of this type have an array of cells or individual detector elements which detect the rays that make up the fan-shaped x-ray beam 16 after the rays have been attenuated differentially by having passed through the body of the patient. The detector has an x-ray transmissive window 18' which allows the rays to pass to the array of individual detector elements, not visible, in detector 18.

For performing computed scanned projection radiography, x-ray beam 16 is pulsed on and off at a high rate, such as sixty times per second or even higher, while the patient is being translated longitudinally at a constant speed through the beam. Each time an x-ray beam pulse is projected, a set of signals indicative of the attenuation by a slice of the patient which is in the beam is produced. These signals are provided to a data acquisition system (DAS) symbolized by the block marked 19. The DAS, among other things, preamplifies the signals, converts them to digital form and multiplexes them to a digital computer 20. The computer is programmed with a suitable algorithm to use the attenuation data obtained in the various slices of the anatomy to develop the data with which a visible image of the length of the scanned region can be constructed. The computer delivers the reconstruction data to a display controller 21 of the type commonly used in computed axial tomography systems. A memory, not shown, in the display controller holds the digital signals, representative of picture elements (pixels). As is known, the controller is adapted for reading out the digital pixel signals from the memory matrix on a line-by-line basis and it converts them to corresponding analog video signals for display in the raster scan mode on a television monitor 22. The analog video images may also be recorded in a video disc recorder 23 so the images can be viewed at any future time.

The new dual energy switching system comes into play, for example, when it is desired to produce energy subtracted projection radiography images to enable better visualization of parts of the anatomy such as blood vessels containing some x-ray opaque medium. This technique requires providing a sequence of low and high energy x-ray pulses so that each slice of the body is interrogated by x-ray of both spectra. The system is synchronized in such a manner that the computer is provided with a set of signals for each low x-ray energy pulse and a set for each high energy pulse. The computer can combine the signals corresponding to the low and high energy pulses and provide a set of signals to the display controller for enabling display of the subtracted image on the monitor shortly after the translational scan is completed.

FIG. 2 shows a digital fluoroscopy system which provides another example of a system in which the new switching system may be used. In the digital fluoroscopy system, a patient 25 is supported on an x-ray transmissive table top 26. The x-ray tube, generally designated by the numeral 27, is located beneath the x-ray table 26. A schematically represented collimator 28 defines the x-ray beam field. The x-ray tube comprises an anode 29, an electron emissive filament 30 and a control element or grid 31. The x-ray power supply is symbolized by the block marked 24 and would include the dual energy switching system which will be described in detail later.

The system in FIG. 2 is designed for performing both temporal and energy subtracting digital fluoroscopy. The operation in the dual energy subtraction mode will now be described to illustrate the system concepts. The x-ray tube is controlled to provide pairs of low energy and high energy x-ray pulses in a repeatable sequence. Pulsed beams in a pair fall on the input screen 32 of an x-ray image intensifier 33. The image intensifier converts the consecutive high and low or low and high energy x-ray images to a series of minified visible images which appear on a phosphor screen 34. A collimating lens 35 is aligned with the phosphor screen and with the input lens of a television camera 36. The television camera is operated synchronously with the x-ray pulses to produce analog video waveforms representative of the respective low and high energy x-ray pulses. The analog signals are transmitted by way of a bus 37 to an analog-to-digital (A/D) converter 38. The converted image data corresponding with a pulse at one energy is delivered to a first memory 39 and the data representative of an image at the other x-ray energy is transmitted to a second memory 40. As soon as the first memory 39 is loaded, the next x-ray pulse occurs and the second memory is loaded. The picture element (pixel) data for both images are provided to a computer 41 which is operative to combine the pixel data representative of the low and high x-ray energy images and to produce a matrix of subtracted pixel signals. The signals representative of the subtracted images may again be provided by means of a bus 42 to a display controller 43. As in the previously described system, a display controller converts the digital pixel-representative signals to corresponding analog video signals on a line-by-line basis for driving a television monitor 44 on whose screen the subtracted image is displayed. A video disc recorder 45 can be supplied with the output video signals to enable future display of the subtracted images on the monitor.

The first embodiment of the power supply and new dual x-ray energy switching system which may be used in the described systems and other systems will now be described in reference to FIG. 3. In this figure, the x-ray tube power supply comprises a variable three-phase autotransformer which is so labelled and is represented by the block marked 50. The ac power lines leading to the 3-phase autotransformer are marked 51. A tap switch mechanism 52, is provided for switching taps on the autotransformer to provide any desired output voltage. The output lines 53 from the autotransformer are run through a primary disconnect switch 54 which, in turn, supplies the Y-connected primary winding of a 3-phase transformer 55. Typically, the transformer will have a Y-primary and a delta-Y connected secondary winding. The output lines 56 and 57 of the transformer are connected to full-wave rectifier bridges 58 and 58', respectively. The rectifier bridges are series-connected and a point 59 between them is grounded. This is a good place to locate the meter 59' which measures the mA flowing through the x-ray tube since it is desirable to have meters at ground potential in the interest of safety. The total dc output voltage from the rectifiers appears between lines 60 and 61. The voltages between line 60 (+HV) and ground point 59 and between line 61 (−HV) and ground point 59 may be considered to be about equal to each other for present purposes and to be equal to about one-half of the total voltage although perfect symmetry is not absolutely necessary. The portion of the power supply described thus far is commonly used in x-ray systems. Typically, the maximum total no-load voltage between lines 60 and 61 may be 150 kilovolts or whatever maximum voltage one may want on the x-ray tube in a particular case. Thus, with the point intermediate of lines 60 and 61 being grounded, positive lines 60 would be at about 75 peak kilovolts (kVp) above ground and negative line 61 will be at 75 kVp below ground potential at the maximum voltage of the system in this numerical example. As is known, having the power line voltages symmetrical or nearly so with respect to ground reduces the insulating requirements of the system.

The x-ray tube is designated generally by the numeral 62. It comprises an evacuated envelope 63, an anode target 64, a thermionic filament 65 and a control element or grid in the form of a focusing cup 66. The metal focusing cup 66 is shown in greater detail in FIG. 4. It has a stepped recess 67 which shapes the electric field around the filament 65 for focusing purposes. The filament is a helical coil of wire which is viewed axially in FIG. 4. The lead wires 68 and 69 for passing current through filament 65 run through an insulator 70.

As shown in FIG. 3, filament 65 is supplied from the secondary winding of a filament transformer 71 whose primary winding is energized from a filament current control logic circuit symbolized by the block marked 72. The current control is basically conventional in that it permits adjusting the magnitude of the current through the filament for setting the temperature of the filament and, hence, its maximum electron emissivity. The maximum amount of current that can flow between anode 64 and filament 65 of the x-ray tube depends on filament temperature, as is well known.

The positive high voltage, +HV, is applied to the x-ray tube anode 64 by way of line 60 which has an adjustable resistor 74 in it. The negative high voltage, −HV, line 61 also has an adjustable resistor 75 in it and it leads to filament 65 by way of lines 76 and 69. The wipers of adjustable resistors 74 and 75 are ganged for being driven concurrently by a reversible motor 77. The total plate or anode impedance of the x-ray tube is the sum of the two resistors plus the internal impedance of the high voltage supply. The settings of adjustable resistors 74 and 75 determines the voltage drop between the anode 64 and cathode filament 65 of the x-ray tube when the tube is conducting. The voltage drop across the tube determines the energy of the x-ray photons produced. Hence, as will be discussed more fully later, these adjustable resistors are involved in determining the voltage drop across the x-ray tube for the low and high energy x-ray pulses and, in conjunction with the control element biasing voltages, the adjustable resistors are determinative of the current that will flow through the x-ray tube during the low and high energy pulses. The peak voltage drop desired across the x-ray tube itself depends on the anode circuit impedance and is selected by operating motor 77 through the agency of its controller 78 which is marked with the legend kVp select. At least one adjustable resistor 74 or 75 is required but two are used here for the sake of maintaining symmetry.

The manner in which the focusing cup or control grid element 66 is biased to obtain low and high voltage or, low and high energy x-ray photon pulses at different x-ray tube currents will now be discussed. Two negative bias voltage supplies 81 and 82 are provided. Bias supply 81 contains a dc rectifier circuit, not visible, that is supplied with ac through a transformer 83. The supply has a negative voltage line 84 and a positive voltage line 85 leading from it. There is a current-limiting resistor 86 in the loop circuit between the negative and positive terminals of the bias supply. There is also a semiconductor switch means represented by a phototransistor 87 in this loop. A line 88 leads from the negative side of the bias supply 81 to control grid or focusing cup 66 of the x-ray tube and there is a grid resistor 89 in this line. Phototransistor 87 is made alternately conductive and non-conductive by triggering it with a pulsed light-emitting diode (LED) 90. When the LED is not emitting light, the phototransistor 87 is non-conducting and the bias voltage from source 81 is applied to focusing cup 66. When LED 90 is emitting, phototransistor 87 becomes conductive and short-circuits or shunts the bias voltage of supply 81 from the control grid or focusing cup 66. Resistor 86 limits the short circuit current to a tolerable value. There is a diode 91 for providing a path between bias voltages supply wire 88 and the other bias supply which includes bias voltage supply source 82.

Bias voltage source 82 and its associated circuitry is similar in construction to the source and circuitry just described although it may be set to provide a bias voltage of different value. Bias source 82 has a negative output line 94 and a positive voltage output line 95. There is a current-limiting resistor 96 in the negative line. This resistor is in a circuit loop which includes semiconductor switch means represented by a phototransistor 97 that connects to the positive side of bias voltage supply 82 by way of line 95. An LED 98 is provided for triggering phototransistor 97 from a non-conductive state to a conductive state whereupon it will shunt or short-circuit the bias supply 82. A diode 99 is connected across the emitter and collector of phototransistor 97. Bias voltage source 82 is supplied with ac through a transformer 100. Transformers 83 for bias supply 81 and 100 for bias supply 82 are provided with primary voltages from a bias control circuit which is symbolized by the block marked 101. Bias control allows for setting the voltages desired from bias voltage sources 81 and 82.

The phototransistors 87 and 97 are triggered on an off by pulsing LEDs 90 and 98 to produce the desired low energy and high energy x-ray pulse levels and durations. The triggering circuit for the LEDs is symbolized by the block 102 which is labelled bias pulse on/off control.

When both LEDs 90 and 98 are turned off, both semiconductor switch means 87 and 97 are non-conductive and the two negative bias voltages from sources 81 and 82 are not shunted and are additive to produce a sufficiently high bias voltage on focusing cup 66 to cut off electron emission from filament 65 in which case the x-ray tube is non-conductive and no x-rays are produced. When only LED 90 is energized, bias voltage V1 from source 81 is shunted leaving only the bias voltage V2 from source 82 effective in which case a predetermined current will flow through the x-ray tube and there will be a particular voltage drop across it, thus providing an x-ray pulse at one energy level. If LEDs 90 and 98 are both energized at the same time, both bias supplies will be shunted by the switch means becoming conductive, resulting in near zero bias voltage being applied to the control electrode or focusing cup 66 of the x-ray tube. This will result in a different amount of current through the x-ray tube and a particular voltage drop across it, thus providing an x-ray pulse at a different level.

Voltage drops between the anode and cathode of the x-ray tube and the current through the tube, if any, under the various biasing conditions just discussed are established in accordance with the dynamic characteristics of the x-ray tube with various load lines being drawn on the plot. One of the load lines which, as in FIG. 8, will serve as a basis for illustration is marked 105. Any load line represents variation of the anode current with voltage for a selected load resistance. Load line 105, like the others next to it represents the resistive values of adjustable resistors 74 and 75 in FIG. 3 plus the internal impedance of the high voltage generators including their associated filter circuits 106 and 107. In FIG. 8, typical bias voltage lines are labelled, for the sake of this example, with the negative voltage they represent. The ordinate of the plot represents current through the x-ray tube and the abscissa represents voltage drop across the x-ray tube. Although it does not appear on the plot, the load lines intersect the abscissa axis at a peak kilovoltage of 150 kilovolts in this example but, in any case, the intersection would occur at a voltage corresponding with the no-load voltage between high voltage lines 60 and 61. In other words, the maximum voltage applied across the x-ray tube under no-load conditions is the power supply voltage which is 150 kVp in this numerical example. Using load line 105 as an example, with the bias voltage V2 from source 82 set at −1800 volts, the load line intersects this bias voltage line at an x-ray tube current of 250 mA and 135 kVp drop across the tube. This is the mA and kVp of the x-ray tube when bias voltage V1 is shunted and only bias voltage V2 from source 82 is effective.

With both bias voltages being shunted, nearly zero voltage will be applied to the focusing cup electrode 66 of the x-ray tube. Referring to the characteristic curves, one may see that the x-ray tube current will now be 850 mA and the kVp will drop to about 75 kVp almost instantly. Only the small capacitance of the high voltage circuit will affect the rate of decay and this is insignificant. It is important to note that an advantage has been achieved over prior art x-ray tube grid controls in that when the voltage drop across the x-ray tube is high a particular current flows through the tube. On the other hand, when the low energy x-ray pulse and correspondingly lower voltage drop occurs across the x-ray tube, the current through the tube is higher than that at the higher kVp which is desirable for imaging purposes. Various load lines can be obtained by adjusting resistors 74 and 75 so that almost any practical combination of x-ray tube voltages and current can be obtained for the low and high energy x-ray pulses.

Figure 9:
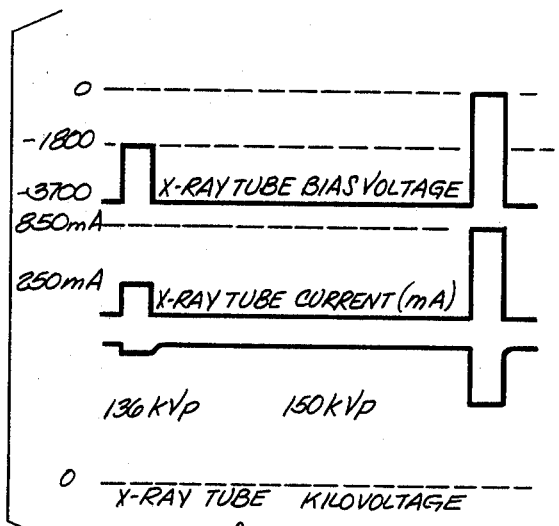
FIG. 9 shows the x-ray tube currents and x-ray tube voltage drops for one set of supply voltages and bias voltages, this figure being provided for illustration and not as a limitation.

If only LED 98 is turned on, then a third operating point could be established. Pulsing the two LEDs in proper sequence, this is, first LED 90 and then both LEDs 90 and 98, will result in alternate x-ray pulses of two different energy levels as shown in FIG. 9. In this figure, the relationships between the various applied voltages, bias voltages and x-ray tube currents are shown for the illustrative values which were just discussed. If a third bias supply and controlling circuitry is added in series with the previous two, a flexible method of generating three x-ray spectra is produced.

The frequency or rate of low and high energy x-ray pulses produced and the intervals between the pulses depends on the sequence and rate at which the LEDs 90 and 98 are pulsed and this is determined by the bias pulse control or triggering system 102 which can be devised by any skilled electronics designer, and need not be described in detail.

When the computed projection radiographic system depicted in FIG. 1 is operated in the energy subtraction mode, the low and high energy pulse frame is represented by the FIG. 5 timing diagram. Pulses at alternating high and low kilovoltage are produced in a regular sequence. By way of example, the low and high energy x-ray pulse durations are typically 1 to 6 ms. The time interval between pairs of pulses is very small. Pulse rates of 120 pps or greater can be easily achieved with the described system.

FIG. 6 represents the timing diagram for production of low energy and high energy x-ray pulse pairs that are more applicable to the digital fluoroscopy system depicted in FIG. 2. In this system, one might elect to have a substantial amount of time such as one second between pulse pairs and resulting subtraction images. However, the time separating the low and high energy pulses of a pair is small, for example, 1/20 sec.

The FIG. 3 embodiment just described wherein various load lines are obtained by simply adjusting resistors 74 and 75 has been proved to be satisfactory in practical application and it is meritorious in that it is relatively easy and inexpensive to implement. A modified embodiment, shown in FIG. 7, provides a means for electronically controlling the effective resistance in series with the x-ray tubes. This is accomplished by replacing adjustable resistors 74 and 75 with high voltage control vacuum tubes 110 and 111. These tubes may be triodes or tetrodes. The use of such tubes allows a more independent choice of techniques for the two pulses since the effective resistance can be changed very quickly. A further benefit of using the high voltage control tubes is that dynamic regulation of kVp during each x-ray pulse is made possible for any case where such regulation might be wanted.

In FIG. 7, the circuitry is the same as in the FIG. 3 embodiment except for the voltage regulator tubes 110 and 111 and the circuit components between them. Parts which are similar in FIG. 7 to those in FIG. 3 are given the same reference numerals.

In FIG. 7, a voltage divider circuit comprised of resistors 112, 113 and 114 is connected across the anode 64 and filament or cathode 65 of the x-ray tube. Resistor 113 is center-tapped and grounded at 115 consistent with the voltage symmetry of the system which was mentioned earlier. The voltage drop across resistor 113 is representative of the voltage drop across the x-ray tube when it is conducting and not conducting. This sensed voltage is provided to a comparator 116 for comparison with a reference voltage, corresponding with desired kVp as suggested by the arrowheaded line marked 117. Control grid bias voltage sources 118 and 119 are provided for altering conductivity of regulator tubes 110 and 111, respectively. The regulator tubes illustrated in this example are tetrodes and thus have two control grids. Comparator 116 develops an error signal if the voltage drop across the x-ray tube results in a voltage across resistor 113 that leaves difference between that voltage and the reference voltage. The error signal is coupled through a pair of opto-isolators 120 and 121, to grid voltage control devices 122 and 123. The control devices respond to the error signals by adjusting the grid bias voltage source output in real-time. In other words, as is well known, the negative bias voltage on the regulator tube control grids is constantly regulated or adjusted up or down during an x-ray pulse in response to error signals. This results in altering the impedance of the regulator tubes and, hence, maintenance of a constant voltage drop across the x-ray tube. Adjustment stops when null is reached, that is, when the sum of the voltage drop across the x-ray and regulator tubes is such that there is no error voltage or difference between the x-ray tube voltage which is sampled with resistor 113 and the kVp reference voltage.

Figure 10:
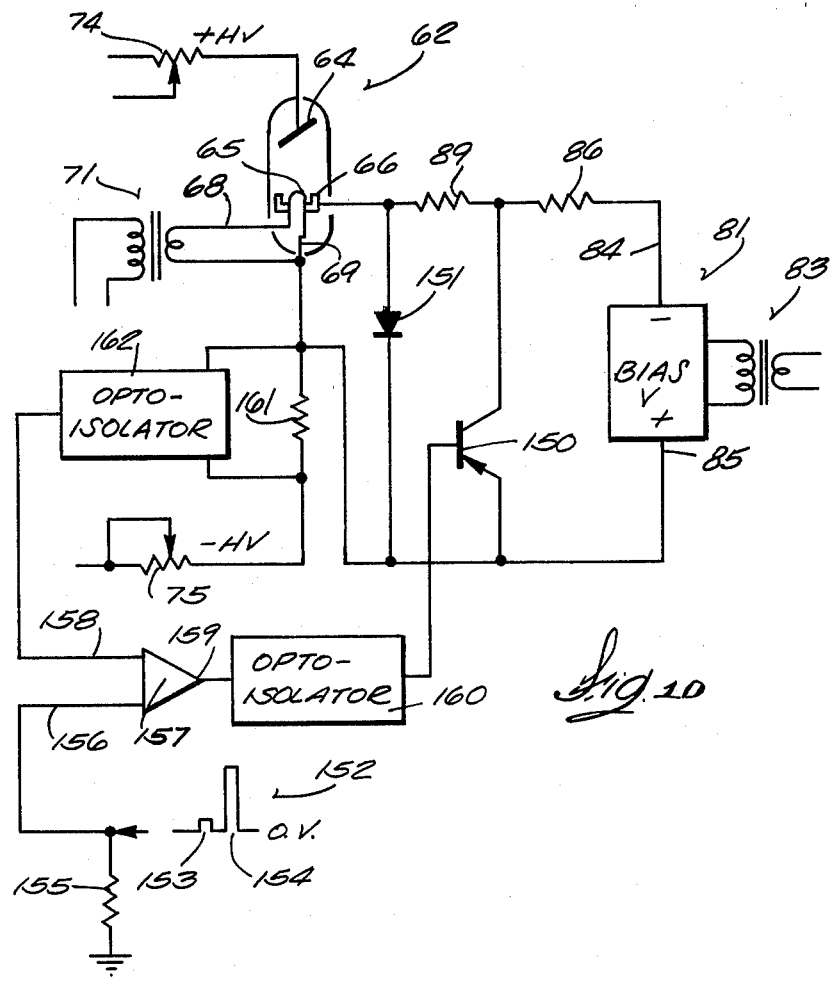
FIG. 10 is an alternative embodiment of the dual energy switching system.

FIG. 10 is an alternative system for causing an x-ray tube to emit pulsed beams at any practical energy level, that is, with any desired voltage drop across the tube, and at selected x-ray intensities, that is, with any desired current level through the tube.

In FIG. 10, parts which are similar to those appearing in FIGS. 3 and 7 are assigned the same reference numerals.

In FIG. 10 only one bias voltage source 81 is used. It is supplied with ac through a transformer 83 and includes a rectifier circuit, not shown, which results in a negative dc bias voltage appearing on output line 84 and a positive voltage on line 85. The voltage between output lines 84 and 85 is sufficiently high to cut off current flow through the x-ray 62 when maximum available bias voltage is applied to control electrode 66 of the tube.

Instead of using two bias voltage sources and shunting one or both or neither to obtain two, three or four bias voltages as in the previously described embodiments, the FIG. 10 embodiment alters the conductivity of a shunting circuit in a stepwise fashion to obtain various x-ray tube currents and voltage drops. Thus, a high voltage transistor group, symbolized by the transistor 150, acts as a variable resistance shunt switching device. The transistor is operated in its active region. It is connected across bias voltage source output lines 84 and 85 in a shunting loop which includes short circuit current limiting resistor 86. The conductivity level of transistor 150 or the voltage drop across it determines the negative bias voltage level on the control element 66 of the x-ray tube with respect to the cathode filament 65. The filament is connected to the −HV high voltage source line as in the previously discussed embodiments. A diode 151 protects the transistor against reverse voltage if such should occur.

To obtain high and low energy x-ray pulses, the base-emitter circuit of the transistor is pulsed or driven correspondingly. A variable amplitude and selectable rate pulse generator, not shown, provides the switching pulses for transistor 150. One pair of pulses 152 for example, composed of a low level pulse 153 and a high level pulse 154 in a pulse train is fed through a resistor 155 whose one end is connected to an input 156 of a comparator amplifier 157. The comparator has another input for a reference or feedback signal which will be discussed soon. The control signal from the output 159 of the comparator is coupled to the base of transistor 150 through an opto-isolator When there is no input pulse 153 or 154 occurring, that is, with zero volts on comparator input 156, transistor 150 is highly forward biased and fully turned on. This shunts the bias voltage and results in substantially zero voltage on x-ray tube control element 66 relative to the filament. Thus, during the interpulse interval, the current through the x-ray tube and the voltage drop across it will depend on the load line (see FIG. 8) which has been established by setting the anode circuit resistor values, such as resistors 74 and 75. Assuming the no load high voltage (+HV) is constant in a given situation, one may see in FIG. 8 that a variety of x-ray tube currents and voltage drops or anode voltages can be obtained by operating on the proper load line when the bias voltage on the x-ray tube is substantially zero. With zero bias voltage, x-ray tube current will be relatively high and voltage drop across the tube will be relatively low which is desirable for reasons given earlier.

With a little more positive triggering pulse such as pulse 153 occurring, transistor 150 switches to a lower conductivity level in which case it shunts less of the bias supply 81 voltage and control element 66 becomes more negative relative to filament 65. Reference to the characteristic curves in FIG. 8 shows that, for whatever load line is being used, the x-ray tube voltage drop will be higher (compared to the previous zero bias voltage state) and the x-ray tube current will decrease which is desirable.

Another higher amplitude triggering pulse, such as the one marked 154, would make transistor 150 even less conductive in which case the x-ray tube 63 would have an even more negative bias voltage applied to its control element 66. Pulse 154 could have sufficient amplitude to cut off current flow through the x-ray in cases where x-ray pulses at only two energy levels, that is, a low and a higher energy level and respectively high and lower currents or x-ray intensities are required. However, it should be evident that various pulse amplitude steps, higher and lower than trigger pulse 153, could be provided. This could provide many x-ray tube current and voltage drop combinations. Thus, the data representative of images at various x-ray tube energy levels can be obtained within a very short interval and multiple subtractions could be performed to eliminate otherwise confusing background anatomy and to emphasize particular anatomy such as iodine infused blood vessels.

Dynamic regulation or real-time regulation of the x-ray tube current is also obtained with the FIG. 10 system by using a feedback circuit. This circuit includes a resistor 161 through which the x-ray tube current flows during each pulse. A voltage drop dependent on current amplitude is produced across resistor 161 during a pulse. By means of an optoisolator 162, this voltage is coupled to the reference voltage input 158 of comparator 157. Thus, if x-ray tube current tends to go above or below what it should be for bias voltages which are supposed to be determined by the amplitudes of the triggering pulses 152, the current error is sensed and the trigger pulses from comparator output 159 are modified. This results in a real-time change in the conductivity of transistor 150 and in the bias voltage in a direction that results in nulling the error.

Shunting or diversion of the bias voltage in FIG. 10 is accomplished with the variable impedance semiconductor or transistor switch having its collector-emitter circuit connected across the bias source as in a shunt regulator. Those skilled in the art will appreciate that the collector-emitter circuit could be connected in the shunting loop between resistors 86 and 89, for example comparable to a series regulator. The base of the transistor could then have the trigger pulses applied to it.

Although illustrative embodiments of the new dual energy x-ray tube biasing system have been described in detail and although only three applications of the system have been given, such description is intended to be illustrative rather than limiting, for the invention may be variously embodied and used and is to be limited only by interpretation of the claims which follow.

We claim:

1. A system for controlling an x-ray tube to emit alternate low and high photon energy x-ray pulses whose photon energy is determined by the voltage drop across the tube during the pulse and whose intensity is dependent on the current passing through the tube during respective pulses, comprising:
   an x-ray tube having an anode, a filament and a control element,
   a high voltage dc source and a circuit for coupling the positive output of the source to the anode and the negative output to the filament,
   adjustable impedance means in said circuit for inserting a selected amount of impedance in addition to the impedance of the source, the voltage drop developed in said circuit by said adjustable impedance means being a function of the current flowing in the circuit between the anode and filament of the x-ray tube,
   at least one dc bias voltage source having a negative output coupled to said x-ray tube control element and a positive output coupled to said x-ray tube filament,
   a shunting circuit including semiconductor switch means connected between the negative and positive outputs of said bias voltage source and between said control element of the x-ray tube, said switch means having a control element, and
   means for applying signals to the control element of the switch means for altering the conductivity of said switch means periodically for said switch means to shunt substantially all or portions of said bias voltage from the control element of the x-ray tube and thereby produce corresponding voltage drops and currents in said x-ray tube,
   shunting all or a major portion of the negative bias voltage from the control element of the x-ray tube causing said tube to conduct high current and said impedance means to develop a higher voltage drop such that there is a correspondingly lower voltage drop between the x-ray tube anode and filament, and
   shunting a lesser portion of the negative bias voltage from the control element of the x-ray tube causing the tube to conduct low current and said impedance means to develop a lower voltage drop such that there is a correspondingly higher voltage drop between the x-ray tube anode and filament.

2. The system defined in claim 1 wherein said adjustable impedance means comprises adjustable resistor means interposed between the negative output of said high voltage source and said filament and adjustable resistor means interposed between the positive output of said high voltage source and the x-ray tube anode.

3. The system set forth in claim 2 wherein:
   said adjustable resistor means each comprise a voltage regulator tube having a plate, a cathode and a control grid, the plate of one tube being coupled to the positive side of said high voltage source and the cathode of the one regulator tube being connected to the anode of said x-ray tube, the cathode of the other regulator tube being connected to the negative side of said high voltage source and the plate of said other tube being connected to the filament of said x-ray tube,
   means for providing a sample voltage representative of the voltage drop across the anode and cathode of the x-ray tube when it is conducting,
   means for providing a selected reference voltage representative of the desired voltage drop across the x-ray tube,
   comparator means operative to compare said sample voltage and reference voltage and to produce an error signal representative of the difference between said sample and reference voltages, a source of grid biasing voltage for each of said regulator tubes, and means for controlling said grid biasing sources, respectively, responsive to said error signal by adjusting the bias voltage to thereby after the resistance of the regulator tubes and the voltage drop across them as required for maintaining a predetermined voltage drop across the x-ray tube.

4. The system defined in any of claims 1, 2 or 3 including:

means for coupling signals including pulse signals to the switch means control element, said pulse signals having different amplitudes, said switch means responding to said pulse signals by altering its conductivity correspondingly for the durations of the pulse signals.

5. The system defined in claim 1 wherein:

said adjustable impedance means is adjustable to provide various load lines on a plot of the dynamic characteristics of the x-ray tube in the circuit, said plot indicating the voltage drop across the tube and corresponding tube current for various negative bias voltages on said x-ray tube control element, the bias voltages which are applied to said control element for x-ray pulses at selected energies being determined, respectively, in accordance with the value of the bias voltage curve on which the desired tube current, voltage drop and load line are coincident.

6. A system for controlling an x-ray tube to emit high and low energy x-ray pulses, comprising:

an x-ray tube having an anode, a filament and a control element, a high voltage dc source and a high voltage supply circuit for coupling said anode to the positive side of the source, said circuit and source having a predetermined impedance, first and second dc bias voltage sources for providing negative bias voltage of predetermined values, the negative side of said first bias voltage source being coupled to said control element and the positive side being coupled to the negative side of said second source and the positive side of the second bias voltage source being coupled to said filament, whereby said bias voltages are additive and can apply sufficient negative bias voltage to said control electrode to cut off current flow through the x-ray tube, a first shunting circuit including first switch means connected between the negative and positive sides of the first bias voltage source and a second shunting circuit including second switch means connected between the negative and positive sides of the second bias voltage source, means for putting the respective switch means selectively in conductive or nonconductive states independently of each other such that if neither switch means is conductive the sum of the bias voltages is applied to said control electrode for cutting off current flow through said x-ray tube, if one of said switch means is conductive and the other is nonconductive the conductive switch means will shunt one bias source between whose sides it is connected and the nonconductive switch means will enable the bias voltage from the other source to be applied to said control element for causing predetermined low current flow through the tube and a correspondingly low voltage drop due to said predetermined impedance in said circuit and source such that there is a higher voltage drop between the anode and filament of said tube, and if both of said switches are conductive both bias sources will be shunted to substantially remove bias voltage from said control element to thereby cause predetermined higher current flow through the tube and a correspondingly higher voltage drop due to said predetermined impedance in said circuit and source such that there is a low voltage drop between the anode and filament of said tube.

7. The system defined in claim 6 wherein said high voltage supply includes a transformer and first and second rectifier bridge means having ac input means supplied from the transformer and providing positive and negative source voltage output means across which said high voltage supply circuit is connected, a point in the dc circuit between said rectifier means being grounded such that the voltage at the positive output means is above ground potential and the voltage at the negative output means is below ground potential, and adjustable resistor means interposed, respectively, in said circuit between said x-ray tube anode and said positive output means in said circuit between the filament and said positive output means.

8. The system defined in claim 6 including:

an adjustable resistor means in said high voltage supply circuit for developing a part of said predetermined impedance.

9. The system set forth in claim 8 wherein:

said adjustable resistor means each comprise a voltage regulator tube having a plate, a cathode and a control grid, the plate of one tube being coupled to the positive side of said high voltage source and the cathode of the one regulator tube being connected to the anode of said x-ray tube, the cathode of the other regulator tube being connected to the negative side of said high voltage source and the plate of said other tube being being connected to the filament of said x-ray tube, means for providing a sample voltage representative of the voltage drop across the anode and cathode of the x-ray tube when it is conducting, means for providing a selected reference voltage representative of the desired voltage drop across the x-ray tube, comparator means operative to compare said sample voltage and reference voltage and to produce an error signal representative of the difference between said sample and reference voltages, a source of grid biasing voltage for each of said regulator tubes, and means for controlling said grid biasing sources, respectively, responsive to said error signal by adjusting the bias voltage to thereby alter the resistance of the regulator tubes and the voltage drop across them as required for maintaining a predetermined voltage drop across the x-ray tube.

10. A system for controlling an x-ray tube to emit alternate low and high photon energy x-ray pulses whose photon energy is determined by the voltage drop across the tube during the pulse and whose intensity is dependent on the current passing through the tube during respective pulse intervals, comprising:

an x-ray tube having an anode, a filament and a control element, a high voltage dc source and a circuit for coupling the positive output of the source to the anode and the negative output to the filament, an adjustable device in said circuit for inserting a selected amount of impedance in addition to the impedance of said source, first and second sources for providing predetermined bias voltages, said sources being connected in series and the negative output of the first source being connected to said x-ray tube control element and the positive output of the second source being connected to said filament, circuits including switch means respectively connected between the negative and positive outputs of the first and second bias voltage sources, said switch means being selectively operable between nonconductive states wherein they do not shunt the bias voltage source to which they are connected to enable the bias voltage to be applied to said control element and conductive states wherein they shunt the respective bias voltage sources, means for selectively controlling said switch means to change between nonconductive and conductive states to thereby permit selective application of the sum of the bias voltages or one or the other of the bias voltages to said control element for affecting the magnitude of the current through the x-ray tube and the voltage drop across said tube for the x-ray pulse produced while the particular bias voltage is applied, controlling said switch means to cause the sum of the bias voltage to be applied to said x-ray tube control element resulting in no current flowing between the anode and filament of said tube controlling said switch means to cause one of the bias voltages to be applied to said control element causing said tube to conduct low current and said impedance to develop a relatively low voltage drop such that there is a correspondingly higher voltage drop between the x-ray tube anode and filament, and controlling such switch means to apply none of the bias voltages to said control element causing said tube to conduct higher current and said impedance to develop a higher voltage drop such that there is a correspondingly lower voltage drop between the x-ray tube anode and filament.

11. The system defined in claim 10 wherein said adjustable impedance device is an adjustable resistor means.

12. The system defined in claim 10 wherein:
said adjustable impedance means is a voltage regulator tube having an anode and cathode connected serially in said circuit and having a control grid,
a bias voltage source coupled to said control grid, said regulator tube responding to variations in the magnitude of the bias voltage by varying its impedance correspondingly.

13. The system defined in claim 10 wherein:
said switch means in the circuits for shunting the bias voltage sources are light responsive switches,
a light-emitting element optically coupled to each of said light responsive switch means,
means for selectively activating said light emitting elements at a repetition rate and for durations corresponding to the rate and duration of the x-ray pulses desired.

14. The system defined in claim 9 wherein:
said adjustable impedance device is adjustable to provide various load lines on a plot of the dynamic characteristics of the x-ray tube in said circuit, said plot showing the voltage drop across the tube and corresponding tube current for various negative bias voltage curves on the control element, said bias voltages for said high and low energy pulses being determined, respectively, in accordance with the value of the bias voltage curve on which the desired tube current, voltage drop and load line are coincident.

* * * * *

UNITED STATES PATENT AND TRADEMARK OFFICE
CERTIFICATE OF CORRECTION

PATENT NO. : 4,361,901

DATED : November 30, 1982

INVENTOR(S) : Herbert E. Daniels; Frank Bernstein; Norbert Pelc; Thomas Lambert

It is certified that error appears in the above—identified patent and that said Letters Patent is hereby corrected as shown below:

Column 13, Line 11, Claim 4, "claims 1, 2 or 3" should read -- claims 1, 2, 3 or 5--

Signed and Sealed this

Thirtieth Day of August 1983

[SEAL]

Attest:

GERALD J. MOSSINGHOFF

Attesting Officer         Commissioner of Patents and Trademarks